United States Patent [19]

Kondo et al.

[11] 4,221,915

[45] Sep. 9, 1980

[54] PROCESS FOR PREPARING THIOPHENE DERIVATIVES AND THIOPHENE DERIVATIVES OBTAINED THEREBY

[75] Inventors: Kiyoshi Kondo, Yamato; Daiei Tsunemoto, Sagamihara; Tamotsu Fujisawa, Yamato, all of Japan

[73] Assignee: Sagami Chemical Research Center, Tokyo, Japan

[21] Appl. No.: 885,261

[22] Filed: Mar. 10, 1978

[30] Foreign Application Priority Data

Mar. 11, 1977 [JP] Japan .................................. 52-26049
Mar. 11, 1977 [JP] Japan .................................. 52-26050

[51] Int. Cl.$^3$ .................... C07D 333/16; C07D 333/24
[52] U.S. Cl. ......................................... 549/78; 549/79
[58] Field of Search .................. 260/332.2 A; 549/78, 549/79

[56] References Cited

U.S. PATENT DOCUMENTS 3,560,525  2/1971  Kaltenbronn ................ 260/332.2 A

OTHER PUBLICATIONS

Hartough, "Chem of Hetero Comp.", Thiophene and Der. (1952), p. 189.
Reeve, J. Amer. Chem. Soc., 83, 2755 (1961).
Wagner, "Synth Org. Chem.", (1965), p. 8.

*Primary Examiner*—A. Siegel
*Attorney, Agent, or Firm*—Frishauf, Holtz, Goodman & Woodward

[57] ABSTRACT

Process for the preparation of a series of thiophene derivatives, from which 2-thiopheneacetic acid derivatives can easily be prepared, in high yields and selectivity by using substituted or unsubstituted thiophenes as the starting materials by easy operations. 2-Thiopheneacetic acid derivatives are very useful compounds as the chemical modifier of penicillin and cephalosporin. Novel compounds, i.e. α-arylthio-2-thiopheneacetic acids are also disclosed. These compounds are useful as the intermediates of the synthesis of 2-thiopheneacetic acids.

15 Claims, No Drawings

PROCESS FOR PREPARING THIOPHENE DERIVATIVES AND THIOPHENE DERIVATIVES OBTAINED THEREBY

BACKGROUND OF THE INVENTION

1. Field of the Invention

The present invention relates to a process for preparing thiophene derivatives and novel compounds obtained thereby and in more detail, this invention relates to a process for preparing a series of thiophene derivatives, from which 2-thiopheneacetic acids having or not having substituent or esters thereof can easily be prepared, in high yields and selectivity by using substituted or unsubstituted thiophenes as the starting materials by easy operations and novel compounds, i.e. α-arylthio-2-thiopheneacetic acids having or not having substituent or esters thereof, obtained in the course of the process.

2. Description of the Prior Art

Prior to the invention, it was known that the compounds represented by the general formula

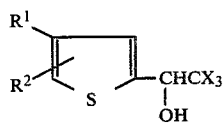

(wherein $R^1$ and $R^2$ are independently selected from hydrogen, halogen or lower alkyl group and X is chlorine or bromine) can be, for example, converted to useful insecticides structurally analogous to DDT by condensation with other aromatic compounds (e.g., H. D. Hartough, "The Chemistry of Heterocyclic Compounds"—Thiophene and its Derivatives, Interscience Publishers, Inc., New York, 1952, p. 189), and the carboxylates of the compounds with the general formula (I) themselves are reported to show insecticidal activities (R. C. Blinn et al., J. Amer. Chem. Soc., 76, 37 (1954)).

The process for the preparation of α-trihalomethyl-2-thiophenemethanols heretofore known to the art comprises the preparation of the Grignard reagent from a 2-bromothiophene and magnesium and then reacting the said reagent with trichloroacetaldehyde to give an α-trihalomethyl-2-thiophenemethanol (J. Amer. Chem. Soc., 71, 2859 (1949)). However, this process cannot be adopted commercially because of the difficulty in the selective synthesis of the starting material, i.e. 2-bromothiophene, and because the process disadvantageously requires an anhydrous condition and necessitates the use of flammable ethers as the reaction medium when preparing the Grignard reagent.

Also, processes for the preparation of α-substituted 2-thiopheneacetic acid derivatives having the general formula

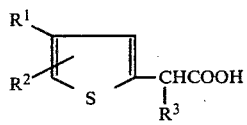

(wherein $R^1$ and $R^2$ are independently selected from hydrogen, halogen or lower alkyl group and $R^3$ is alkoxy group, hydroxyl group or amino group) heretofore known to the art are: (1) the condensation of a 2-thiophenealdehyde with bromoform in the presence of a base (J. Amer. Chem. Soc., 83, 2755 (1961)), (2) the oxidation of a 2-acetylthiophene with selenium dioxide and then treating with an alkali (Arkiv Kemi., 11, 519 (1957)), (3) the preparation of 2-thiophenealdehyde cyanohydrin and then conducting hydrolysis (Japanese Patent Disclosure No. 8775/73), (4) the addition of glyoxylic acid on thiophene (Japanese Patent Disclosure No. 49954/74), etc.

However, the process (1) necessitates the use of expensive bromoform and 2-thiophenealdehyde as the raw materials and the yield of the product is low. The process (2) necessitates the use of expensive and dangerous selenium dioxide and is difficult to adopt as a commercial process. The process (3) requires 2-thiophenealdehyde which is difficultly accessible commercially, and necessitates the use of highly poisonous hydrogen cyanide. Although the process (4) requires a shorter reaction step, yield of the product is low and is thus difficult to adopt as a commercial process.

Further, the process for the preparation of 2-thiopheneglycolic acid by the reduction of 2-thiopheneglyoxylic acid in an alcohol by the use of sodium amalgam was known prior to the invention (F. Ernst, Ber., 19, 3278 (1886)), however, commercial production by the process above is difficult, since the prior synthetic method gives 2-thiopheneglyoxylic acid in relatively low yield, which is required as the starting material.

It was known that the α-substituted 2-thiopheneacetic acid derivatives themselves can be converted to penicillin derivatives having antibiotical activities by reacting them with penicillanic acid derivatives (Cf. e.g. Netherlands Octrooiaanvrage No. 6506584), and 2-thiopheneacetic acids which are the compounds obtainable by replacing the substituent located in α-position of said α-substituted 2-thiopheneacetic acids with hydrogen are very useful as chemical modifier of penicillin and cephalosporin (Cf. J. Amer. Chem. Soc., 84, 3401 (1962)).

The main processes for the preparation of 2-thiopheneacetic acid heretofore known may be classified into three processes described below, according to the starting materials employed: (1) converting 2-chloromethylthiophene to 2-cyanomethylthiophene at first by treating with an alkali cyanide, and then conducting hydrolysis thereof (Japanese Patent Disclosure No. 46063/77); (2) converting by Willgerodt reaction of 2-acetylthiophene with ammonium polysulfide to 2-thiopheneacetamide at first and then conducting hydrolysis thereof (Otto Dann, Ger. Pat. No. 832755 (1952)), (3) (a) reacting potassium cyanide and an ester of chloroformic acid on 2-thiophenealdehyde to form an α-alkoxycarbonyloxy-2-thiopheneacetonitrile, and then conducting catalytic hydrogenation thereof to 2-cyanomethylthiophene, and further conducting hydrolysis thereof (M. J. Soulal, M. C. Woodford, British Pat. No. 1,122,658 (1968); (b) treating the condensation product of 2-thiophenealdehyde and methyl methylthiomethyl sulfoxide with hydrogen chloride in alcohol to form an ester of 2-thiopheneacetic acid and then conducting hydrolysis thereof (Japanese Patent Disclosure No. 46063/77); etc. However, the process (1) includes difficulties in that 2-chloromethylthiophene is difficult to handle because it is unstable, explosive, and is a lachrymatory substance, and also, highly poisonous bis(-chloromethyl) ether is formed as by-product during the preparation of this compound. The process (2) possesses shortcomings in that it requires a high-temperature and high-pressure condition in performing the Willgerodt reaction, and requires severe conditions for the hydrolysis. Also, the process (3) (a) has its demerit in that it necessitates the use of highly poisonous cyanide compounds, and requires many reaction stages, etc. The process (3) (b) in disadvantageous in that it needs attention in handling, and produces sulfur compounds having strong unpleasant odor.

SUMMARY OF THE INVENTION

Accordingly, the object of this invention is to provide a process for preparing a series of thiophene derivatives, from which 2-thiopheneacetic acid having or not having substituent or esters thereof can easily be prepared, in high yields by using substituted or unsubstituted thiophenes as the starting material by easy operations, and novel compounds, i.e. α-arylthio-2-thiopheneacetic acids having or not having substituent and esters thereof are obtained in the course of the process.

To assist in understanding this invention, the process and products of the invention are given in a chemical scheme:

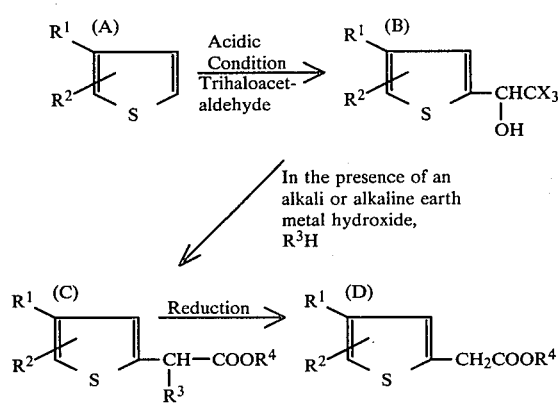

In the scheme shown above, $R^1$ and $R^2$ are independently selected from the group consisting of hydrogen, halogens and alkyl groups; $R^3$ is selected from the group consisting of alkoxyl groups, hydroxyl groups, amino groups, alkylthio groups and arylthio groups; $R^4$ represents hydrogen or an alkyl group; and X represents halogen atom and preferably one selected from the group consisting of chlorine, bromine and iodine.

In the scheme shown above, compounds (C) are novel compounds when $R^3$ is an arylthio group and the compounds are useful as an intermediate of the synthesis of the final product (D) of the process of this invention, i.e. 2-thiopheneacetic acids having or not having substituent or esters thereof.

In this invention, the process to prepare compounds (C) via compounds (B) from compounds (A) is developed by the inventors through intensive studies toward establishing a process which overcomes the disadvantages found in the prior art aforementioned and selectively affords only the desired compounds, and found that the desired compounds (B) can be prepared in a good yield by treating under an acidic condition, a substituted or unsubstituted thiophene with a trihaloacetaldehyde both of which are easily obtainable as industrial raw materials.

That is, the first object of this invention is to provide a process for preparing 2-thiopheneacetic acid derivatives (C) represented by the general formula

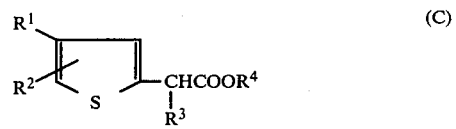

which comprises reacting a thiophene derivative (A) having the general formula

with a trihaloacetaldehyde represented by the general formula $CX_3CHO$ under an acidic condition to obtain an α-trihalomethyl-2-thiophenemethanol (B) having the general formula

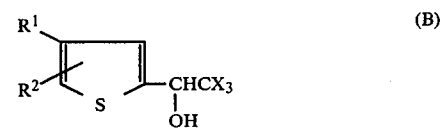

It is preferred to establish the acidic condition by the use of a Lewis acid, and then further reacting the reaction product thus obtained with a compound having the general formula $R^3H$ in the presence of an alkali or alkaline earth metal hydroxide and if desired, the reaction product is further esterified in any suitable manner known in the art, such as reacting with an alcohol having the general formula $R^4OH$ (wherein $R^1$, $R^2$, $R^3$, $R^4$ and X are as defined before).

The compounds (C) thus obtained can easily be converted to compounds (D), i.e. 2-thiopheneacetic acids having or not having substituent or esters thereof which are the final products of the process of this invention by reduction.

The second object of this invention is, therefore, to provide a process for the preparation of 2-thiopheneacetic acids represented by the general formula:

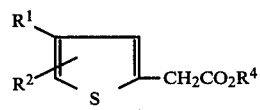

which comprises reacting a thiophene having or not having substituent represented by the general formula

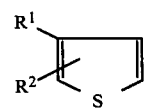

with a trihaloacetaldehyde represented by the general formula $CX_3CHO$ under an acidic condition to prepare an α-trihalomethyl-2-thiophenemethanol represented by the general formula

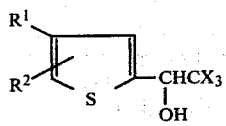

at first, then reacting the α-trihalomethyl-2-thiophenemethanol thus obtained with a compound represented by the general formula R³H in the presence of an alkali or an alkaline earth metal hydroxide, and if desired, the product is further esterified by reacting with an aliphatic alcohol to obtain an α-substituted 2-thiopheneacetic acids represented by the general formula

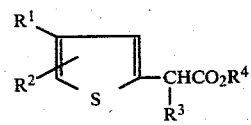

and then the α-substituted 2-thiopheneacetic acid thus prepared is subjected to hydrogenation (wherein R¹, R², R³, R⁴ and X are as defined before).

The third object of this invention is to provide novel compounds, i.e. α-substituted 2-thiopheneacetic acids represented by the general formula

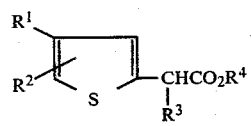

(wherein R³ represents an arylthio group; R¹, R² and R⁴ are defined before).

Other object of this invention will become apparent during the following detailed description of the invention.

DETAILED DESCRIPTION OF THE INVENTION

As examples of one of the starting materials of the present invention represented by the general formula

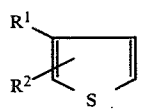 (A)

(wherein R¹ and R² are as defined before), thiophene, 2-chlorothiophene, 2-bromothiophene, 2,3-dichlorothiophene, 2-methylthiophene, 2-ethylthiophene, 2-methyl-3-chlorothiophene, 2-chloro-3-methylthiophene, etc. may be cited. As examples of the other starting compound represented by the general formula CX₃CHO (wherein X is as aforementioned), trichloroacetaldehyde, tribromoacetaldehyde, etc. may be cited.

The present invention requires as the indispensable matter to treat the two starting materials described above under an acidic condition, and the acidic condition can be established by the presence of an inorganic acid such as sulfuric acid and phosphoric acid, an ion-exchange resin in which such acid is supported on a polymer substance, or a Lewis acid such as titanium tetrachloride, stannic tetrachloride, boron trifluoride, iron chloride and aluminum chloride. The use of a Lewis acid is particularly preferred. It is usually sufficient to use an equimolar amount of such acidic substance, but in the reaction of this kind in general, the reaction may proceed beyond the desired stage in some cases to afford 1,1-dithienylethanes as by-products. It is preferable to conduct the reaction in the presence of titanium tetrachloride and/or a titanium alkoxide in order to prevent or minimize the formation of such by-products. The usual solvents for Friedel-Crafts reactions, namely an aliphatic hydrocarbon such as hexane and heptane, a halogenated hydrocarbon such as methylene chloride and trichloroethane, and carbon disulfide, and, if desired, ethers may be used as the solvent without disadvantage. Usually, the reaction proceeds at room temperature, but if desired, the reaction may be accelerated by heating.

As described above, 1,1-dithienylethanes may be formed as by-products in some cases, and to avoid the formation of such by-products, reaction solvents may be used, or the formation of the by-products may be reduced by adopting a procedure which allows only the starting materials to recycle and come into contact with the catalyst by utilizing the boiling point difference between the starting materials and the products.

Under such conditions as described above, α-trihalomethyl-2-thiophenemethanols (B) above can be formed in high yields. The compounds, after isolation or without isolation, can be used for the treatment of the next step.

The second step comprises the reaction of an α-trihalomethyl-2-thiophenemethanol (B) above with a compound represented by the general formula R³H. As examples of compounds R³H, water, an alcohol such as methanol, ethanol, isopropanol, and butanol, a thiol such as methyl mercaptan, ethyl mercaptan, isopropyl mercaptan, thiophenol, and tolyl mercaptan, and an amine such as ammonia, methylamine, ethylamine, isopropylamine, dimethylamine and diethylamine and the like may be cited.

The second step requires as the indispensable condition, the use of an alkali or an alkaline earth metal hydroxide as the condensation reagent, and the use of sodium hydroxide or potassium hydroxide is preferred from an economical view. It is preferable to use at least 3 molar equivalents of these bases to compounds (B), and the desired compounds (C) can generally be prepared selectively by the use of 3 to 4 molar equivalent amounts of a base. It is preferable to use solvents in conducting the reaction, and when the compound represented by the general formula R³H is an alcohol, for example, an excess of the alcohol R³H may be used as the solvent. When a thiol or an amine is used as the compound represented by R³H, an alcohol may be used as the solvent, and in this case, the thiol or amine react preferentially because of the difference in the reaction rates. As in the case of the first step, the reaction of this step proceeds even at room temperature, but it is preferred to operate the reaction at the reflux temperature of the solvent used in order to accelerate the reaction and to selectively obtain only the desired compounds.

Further, the α-substituted 2-thiopheneacetic acid derivatives (C) prepared in accordance with the process described above can be readily converted to 2-thiopheneacetic acids having or not having substituent or esters thereof (D) by reductive treatment.

With regard to the reductive treatment, it is possible to perform the reduction by the following methods depending upon the kind of the R³ substituent of the general formula (C). Thus, when $R^3$ is an alkoxyl group, a nickel-type catalyst such as Raney-nickel, a palladium-type catalyst such as palladium-charcoal, or a platinum catalyst may be used. These catalysts are commonly used for catalytic hydrogenation reactions of benzyl ethers. Water, acetone, a hydrocarbon solvent or an ether solvent may be exemplified as the solvent. The reaction can be performed at room temperature and under atmospheric pressure. In order to improve the selectivity of the reaction, a mineral acid such as hydrochloric acid and sulfric acid, or a mineral or an organic base such as sodium or potassium hydroxide, sodium or potassium acetate, triethylamine, pyridine, etc. may be added. Besides the catalytic hydrogenation described above, the reduction treatment by the use of hydrogen halide, and particularly hydrogen iodide, red phosphorus and hydrogen iodide (or iodine), or red phosphorus and hydrochloric acid may be used as the general reductive procedure. The reaction is performed, preferably, in a water-acetic acid system, but other solvents such as acetone, hydrocarbon solvents and ether solvents which do not directly affect the reaction may be allowed to co-exist, and the reaction is generally completed by heating under reflux.

When $R^3$ is a hydroxyl group, the reduction method by the use of stannous chloride and hydrochloric acid, and the catalytic hydrogenation method by the use of cooperchromium oxide or molybdenum sulfide may be exemplified as the general reduction method, in addition to the catalytic hydrogenation method and the reduction method by the use of a hydrogen halide as exemplified above in the case of the alkoxyl group derivatives.

When $R^3$ is an alkylthio group or an arylthio group, the conventional reductive desulfurization methods for $\alpha$-thiocarboxylic acids can be used. Namely, the method by the use of a combination of zinc and an acid such as acetic acid, hydrochloric acid, or sulfuric acid, or by the use of aluminum amalgam or zinc amalgam or the method using a nickel-type catalyst such as Raney-nickel, can be utilized.

When $R^3$ is an amino group, the method employing a nickel-type catalyst such as Raney-nickel or a palladium-type catalyst such as palladium-charcoal may be exemplified.

DESCRIPTION OF THE PREFERRED EMBODIMENTS

In the followings, the invention will be explained in more detailed and material fashion by illustration of Examples, however, please note that these Examples are given only for the purpose of illustration and are not to be construed as limiting this invention thereto. Tetramethylsilane was used as the internal standard in NMR measurement and the values were shown by $\delta$, in ppm.

EXAMPLE 1

Thiophene (4.2 g, 50 mmol) and trichloroacetaldehyde (7.35 g, 50 mmol) were dissolved in n-heptane (25 ml). The solution was heated under reflux for 3.5 hr. under a Soxleht apparatus in which Amberlyst 15 (4.2 g) had been placed. After cooling, the n-heptane solution was concentrated, and the residue was purified by distillation to give 2.32 g of $\alpha$-trichloromethyl-2-thiophenemethanol boiling at 98°–100° C./1.0 mmHg.

EXAMPLE 2

To a solution of titanium tetrachloride in methylene chloride (1 molar concentration; 30 ml, 30 mmol), titanium tetraisopropoxide (4.26 g, 15 mmol) was added under an argon atmosphere with stirring and under water cooling. After 10 min., thiophene (2.52 g, 30 mmol) was added and then trichloroacetaldehyde (8.82 g, 60 mmol) was added dropwise during 10 min. with stirring and under ice-water cooling. After the addition was completed, stirring was continued for further 10 min., and then water and methylene chloride were added successively, and the organic layer was separated. The organic layer was washed with water and dried over anhydrous magnesium sulfate. The solution was filtered and, after removal of the solvent by distillation under a reduced pressure with an aspirator, the residue was distilled to form trichloroacetaldehyde isopropyl alcoholate initially and then 5.0 g of $\alpha$-trichloromethyl-2-thiophenemethanol.

Yield: 72% (based on thiophene).

bp: 95°–97° C./0.7 mmHg (Literature value: 140°–142° C./10 mmHg).

IR (cm$^{-1}$): 3425, 1065, 1044, 822 and 710.

NMR (CDCl$_3$): 3.48 (d, J=5 Hz, 1H), 5.40 (d, J=5 Hz, 1H) and 6.88–7.50 (m, 3H).

EXAMPLE 3

Titanium tetraisopropoxide (2.13 g, 7.5 mmol) was dissolved in methylene chloride (10 ml). To the solution, titanium tetrachloride solution in methylene chloride (1 molar solution, 30 ml, 30 mmol) was added. The mixture was cooled to $-70°$ C. and then, trichloroacetaldehyde (8.8 g, 59.7 mmol) was added thereto. Further, 2-chlorothiophene (3.56 g, 30 mmol) solution in methylene chloride (10 ml) was added into the mixture. The mixture was kept at the same temperature under agitation for 1 hr. and then, the temperature was raised slowly to $-10°$ C. The reaction mixture was poured into ice-water and the organic layer was separated. The organic layer was washed with sodium chloride solution in water and dried with magnesium sulfate. After removal of solvent, vacuum distillation was conducted. Thereby, 2,2,2-trichloro-1-(5-chlorothiophene-2)-ethanol (3.52 g, 44%) was obtained.

bp: 94°–100° C./0.15 mmHg

NMR (CCl$_4$): 3.20 (d, J=4 Hz, 1H), 5.20 (d, J=4 Hz, 1H), 6.72 (d, J=4 Hz, 1H) and 6.97 (d, J=4 Hz, 1H).

EXAMPLE 4

Under an argon atmosphere, potassium hydroxide (1.12 g, 20 mmol) was dissolved in methanol (10 ml). A solution of $\alpha$-trichloromethyl-2-thiophenemethanol (1.16 g, 5 mmol) in methanol (3 ml) was added with stirring and under water cooling. After 10 min., the mixture was heated up gradually and heated under reflux for 1 hr. with vigorous stirring. It was cooled to room temperature, most of the solvent was removed by distillation under a reduced pressure, diethylether was then added and the mixture was decomposed with dilute hydrochloric acid. The ether layer was separated and the water layer was extracted with ethyl acetate. The organic layers thus obtained were combined to one layer and was washed with an aqueous solution of sodium chloride and dried with anhydrous sodium sulfate. After filtration, the filtrate was concentrated under a reduced pressure to give 620 mg of $\alpha$-methoxy-2-thiopheneacetic acid.

Yield: 73%.

IR (cm$^{-1}$): 3100, 2925, 1730, 1180, 1100, 880, 845 and 707.

NMR (CDCl$_3$): 3.38 (s, 3H), 5.00 (s, 1H), 6.81–7.40 (m, 3H) and 10.58 (s, 1H).

EXAMPLE 5

Under an argon atmosphere, potassium hydroxide (1.12 g, 20 mmol) was dissolved in methanol (10 ml). Thiophenol (0.6 g, 5.45 mmol) was added to this solution with stirring and under water cooling. After 10 min., a solution of α-trichloromethyl-2-thiophenemethanol (1.16 g, 5 mmol) in methanol (3 ml) was added. After 10 min., the mixture was gradually heated up and was heated under reflux for 2 hr. with vigorous stirring. After cooling to room temperature and after removal of most of the solvent by distillation under a reduced pressure, diethylether was added and the mixture was decomposed with dilute hydrochloric acid. The ether layer was separated, washed with water, and dried with anhydrous magnesium sulfate. After filtration, the filtrate was concentrated under a reduced pressure and the residue was purified by silica gel column chromatography (ethyl acetate: n-hexane=1:4) to give 940 mg of α-phenylthio-2-thiopheneacetic acid as a viscous oil.

Yield: 76%.

IR (cm$^{-1}$): 3060, 1715, 1587, 1485, 1440, 1416, 1253, 750, 705 and 694.

NMR (CDCl$_3$): 5.03 (s, 1H), 6.62–7.60 (m, 8H) and 11.47 (s, 1H).

EXAMPLE 6

Into 20 ml of ethanol, α-trichloromethyl-2-thiophenemethanol (2.32 g, 10 mmol) was dissolved and an aqueous solution of sodium methyl mercaptide (20%, 10 g, 29 mmol) was further added thereto. Into the solution, potassium hydroxide (2.4 g, 36 mmol) solution in ethanol (20 ml) was added in drop-wise. After the addition was completed, the reaction mixture was agitated for 30 min. at room temperature. Thereafter, the temperature was raised to 50° C. and agitation was further conducted for 5 hr. at the temperature, then, the solvent was distilled off under vacuum. The residue thus obtained was dissolved in water and was washed with methylene chloride. After being acidified with hydrochloric acid, extraction was conducted with methylene chloride. After drying of the organic layer with magnesium sulfate, the organic layer was concentrated. Thereby, crude α-methylthio-2-thiopheneacetic acid (1.75 g, 93%) was obtained. After purification with silica gel chromatography, 1.66 g (88%) of pure product was obtained.

NMR (CCl$_4$): 1.98 (s, 3H), 4.67 (s, 1H), 6.75–6.97 (m, 1H), 7.00–7.28 (m, 2H) and 11.95 (s, 1H).

EXAMPLE 7

Into 2.4 ml of water, potassium hydroxide (0.67 g, 12 mmol) and lithium chloride (0.254 g, 6 mmol) were dissolved. Then, into the solution above, α-trichloromethyl-2-thiophenemethanol (0.693 g, 3 mmol) solution in dioxane (2.4 ml) was added and agitation was conducted for 12 hr. at room temperature and for 3 hr. at 80° C. Thereafter, water (20 ml) was added thereto and diethylether was further added into the reaction mixture. The ether soluble part was separated. The water layer was acidified with hydrochloric acid and then, extracted with diethylether. The organic layer was dried with anhydrous magnesium sulfate and was treated with activated carbon and filtered. Thereafter, the filtrate was concentrated and gave 0.246 g of 2-thiopheneglycolic acid as crystals.

Crude yield: 52%.

NMR (CDCl$_3$): 5.47 (s, 1H), 6.80–7.35 (m, 3H) and 8.52 (broad s, 2H).

EXAMPLE 8

α-Phenylthio-2-thiopheneacetic acid (890 mg, 3.56 mmol) was dissolved in acetic acid (6 ml), then zinc dust (350 mg, 5.4 mmol) was added and the mixture was heated under reflux with vigorous stirring. After 30 min., zinc dust (350 mg, 5.4 mmol) was added again, and the mixture was heated under reflux for another 4 hr. with stirring, then cooled to room temperature, and most of the solvent was removed by distillation. Water and ethyl acetate were added and the precipitate was filtered off by the use of celite, and the layers of the filtrate were separated. The organic layer was washed with an aqueous solution of sodium chloride and dried with anhydrous magnesium sulfate. After filtration, the solution was concentrated under a reduced pressure and the crystals thus obtained were further recrystallized from ethyl acetate: n-hexane to give 2-thiopheneacetic acid (430 mg) melting at 62° C. (literature value: 62°–65° C.).

Yield: 85%.

EXAMPLE 9

Red phosphorous (180 mg) and iodine (60 mg) were added to acetic acid (2.85 ml), and the mixture was stirred for 30 min. A solution of water (60 mg) and α-methoxy-2-thiopheneacetic acid (860 mg, 5 mmol) in acetic acid (1.5 ml) was added to this mixture and the resulting mixture was heated under reflux for 2 hr. with vigorous stirring. After cooling to room temperature, water and ethyl acetate were added thereto. After filtering off the precipitate by the use of celite, the organic layer was separated. It was washed with saturated aqueous solution of sodium chloride and dried with anhydrous magnesium sulfate. After filtration, the solution was concentrated under a reduced pressure, and the crystals which remained were recrystallized from ethyl acetate:n-hexane to give 2-thiopheneacetic acid (610 mg) melting at 62° C. (Literature value: 62°–65° C.).

Yield: 86%.

We claim:

1. A process for the preparation of α-trihalomethyl-2-thiophenemethanols of the formula

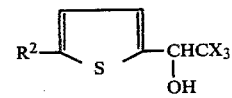

which comprises reacting a thiophene of the formula

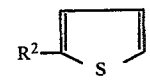

with a trihaloacetaldehyde of the formula CX$_3$CHO under an acidic condition which is established by carrying out said reaction in the presence of an acid selected from the group consisting of (i) an ion-exchange resin comprising an acid supported on a polymer substance, (ii) titanium tetrachloride, and (iii) titanium tetrachloride and titanium tetraisopropoxide, at a temperature between 0° C. and the reflux temperature of the reaction mixture, wherein $R^2$ is hydrogen or a halogen atom; and X is selected from the group consisting of chlorine, bromine and iodine.

2. The process of claim 1, wherein said reaction is carried out in the presence of titanium tetrachloride.

3. The process of claim 1, wherein said reaction is carried out in the present of titanium tetrachloride and titanium tetraisopropoxide.

4. The process of claim 1, wherein said reaction is carried out in the presence of an ion-exchange resin comprising an acid supported on a polymer substance which is used to establish said acid condition.

5. The process of claim 1, wherein said α-trihalomethyl-2-thiophenemethanol product is separated from unreacted starting materials by utilizing the difference between their respective boiling points, and said unreacted starting materials are recycled to react under said acidic condition and said temperature.

6. The process of claim 1, wherein the molar ratio of said trihaloacetaldehyde to said thiophene is between about 1 and 2, and the molar ratio of said acid to said thiophene is not higher than 1.

7. A process for the preparation of α-substituted-2-thiopheneacetic acids of the formula

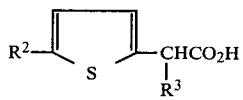

which comprises reacting a thiophene of the formula

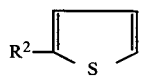

with a trihaloacetaldehyde of the formula $CX_3CHO$ under an acidic condition which is established by carrying out said reaction in the presence of an acid selected from the group consisting of (i) an ion-exchange resin comprising an acid supported on a polymer substance, (ii) titanium tetrachloride, and (iii) titanium tetrachloride and titanium tetraisopropoxide, at a temperature between 0° C. and the reflux temperature of the reaction mixture, to form an α-trihalomethyl-2-thiophenemethanol of the formula

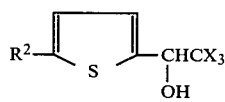

and then reacting said α-trihalomethyl-2-thiphenemethanol with a compound of the formula $R^3H$ in the presence of a hydroxide selected from the group consisting of alkali and an alkaline earth metal hydroxides, at a temperature between room temperature and the reflux temperature of the reaction mixture, wherein $R^2$ is hydrogen or a halogen atom; $R^3$ is selected from the group consisting of alkoxyl groups, hydroxyl groups, alkylthio groups and arylthio groups; and X is selected from the group consisting of chlorine, bromine and iodine.

8. The process of claim 7, wherein said hydroxide is sodium hydroxide or potassium hydroxide.

9. The process of claim 8, wherein 3 to 4 moles of said hydroxide are used per mole of said α-trihalomethyl-2-thiophenemethanol.

10. The process of claim 7, wherein an alcohol or an ether is present as a solvent.

11. The process of claim 7, wherein $R^3H$ is water.

12. The process of claim 7, wherein $R^3H$ is an alcohol.

13. The process of claim 7, wherein $R^3H$ is a thiol and 1 to 3 moles thiol are used per mole of said α-trihalomethyl-2-thiophenemethanol.

14. A process for the preparation of 2-thiopheneacetic acids of the formula

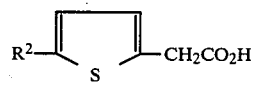

which comprises reacting a thiophene of the formula

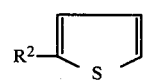

with a trihaloacetaldehyde of the formula $CX_3CHO$ under an acidic condition which is established by carrying out said reaction in the presence of an acid selected from the group consisting of (i) an ion-exchange resin comprising an acid supported on a polymer substance, (ii) titanium tetrachloride, and (iii) titanium tetrachloride and titanium tetraisopropoxide, at a temperature between 0° C. and the reflux temperature of the reaction mixture, to form an α-trihalomethyl-2-thiophenemethanol of the formula

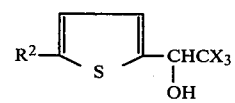

and then reacting said α-trihalomethyl-2-thiophenemethanol with a compound of the formula $R^3H$ in the presence of an alkali or an alkaline earth metal hydroxide at a temperature between room temperature and the reflux temperature of the reaction mixture, to obtain an α-substituted 2-thiopheneacetic acid of the formula

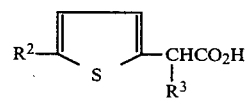

and then hydrogenating said α-substituted 2-thiopheneacetic acid by contacting with zinc and an acid, wherein $R^2$ is hydrogen or a halogen atom; $R^3$ is an alkylthio group or an arylthio group; and X is selected from the group consisting of chlorine, bromine and iodine.

15. A process for the preparation of 2-thiopheneacetic acids of the formula

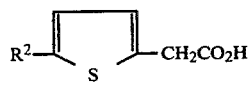

which comprises reacting a thiophene of the formula

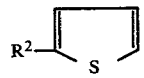

with a trihaloacetaldehyde of the formula $CX_3CHO$ under an acidic condition which is established by carrying out said reaction in the presence of an acid selected from the group consisting of (i) an ion-exchange resin comprising an acid supported on a polymer substance, (ii) titanium tetrachloride, and (iii) titanium tetrachloride and titanium tetraisopropoxide, at a temperature between 0° C. and the reflux temperature of the reaction mixture, to form an α-trihalomethyl-2-thiophenemethanol of the formula

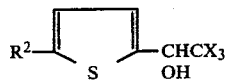

and then reacting said α-trihalomethyl-2-thiophenemethanol with a compound of the general formula $R^3H$ in the presence of an alkali or an alkaline earth metal hydroxide at a temperature between room temperature and the reflux temperature of the reaction mixture to obtain an α-substituted 2-thiopheneacetic acid of the formula

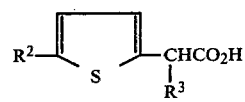

and then hydrogenating said α-substituted 2-thiopheneacetic acid by contacting with iodine and red phosphorus, wherein $R^2$ is hydrogen or a halogen atom; $R^3$ is an alkoxyl group or hydroxyl group; and X is selected from the group consisting of chlorine, bromine and iodine.

* * * * *